(12) United States Patent
Liu et al.

(10) Patent No.: US 10,898,521 B2
(45) Date of Patent: Jan. 26, 2021

(54) ANTIMICROBIAL STRAIN COMPOSITION AND ITS PREPARATION METHOD

(71) Applicants: Amy Li, Katy, TX (US); Jielong Liu, Doveton (AU); Xia Liu, Doveton (AU); Li Wang, Houston, TX (US)

(72) Inventors: Jielong Liu, Doveton (AU); Xia Liu, Doveton (AU)

(73) Assignees: Amy Li, Katy, TX (US); Li Wang, Houston, TX (US); Jielong Liu; Xia Liu

(*) Notice: Subject to any disclaimer, the term of this patent is extended or adjusted under 35 U.S.C. 154(b) by 0 days.

(21) Appl. No.: 16/732,328

(22) Filed: Jan. 1, 2020

(65) Prior Publication Data

US 2020/0222466 A1 Jul. 16, 2020

(30) Foreign Application Priority Data

Jan. 11, 2019 (AU) ................................ 2019100035

(51) Int. Cl.
| | |
|---|---|
| *A61K 35/20* | (2006.01) |
| *A23L 3/3463* | (2006.01) |
| *A61K 31/70* | (2006.01) |
| *A61K 35/57* | (2015.01) |
| *A61K 35/747* | (2015.01) |
| *A61K 36/87* | (2006.01) |
| *C12Q 1/18* | (2006.01) |

(52) U.S. Cl.
CPC .......... *A61K 35/20* (2013.01); *A23L 3/34635* (2013.01); *A61K 31/70* (2013.01); *A61K 35/57* (2013.01); *A61K 35/747* (2013.01); *A61K 36/87* (2013.01); *C12Q 1/18* (2013.01); *A23V 2002/00* (2013.01)

(58) Field of Classification Search
CPC ...... A61K 35/20; A61K 31/70; A61K 35/747; A61K 36/87; A61K 35/57; A23L 3/34635; C12Q 1/18; A23V 2002/00
See application file for complete search history.

(56) References Cited

U.S. PATENT DOCUMENTS 6,953,574 B2 * 10/2005 Sobol .................. A23L 33/17
424/93.45

* cited by examiner

*Primary Examiner* — Louise W Humphrey
*Assistant Examiner* — Anjali Ajit Hirani
(74) *Attorney, Agent, or Firm* — Nz Carr Law Office

(57) ABSTRACT

Here disclosed is a method of preparing an antimicrobial strain composition from milk, a raw egg and a plant part, which includes the following steps: 1) providing a dairy composition comprising milk, a fermentable sugar, and edible starters from each of *Lactobacillus*, *Bifidobacterium* and *Acetobacter*, combining a first aliquot of the dairy composition (part A) with *Rhizopus oryzae*, *Aspergillus niger* and/or *Aspergillus oryzae*, and an edible starter from *Saccharomyces*, and conducting fermentation so as to enable the part A composition to substantially turn into a milk curd, 3) combining a second aliquot of the dairy composition (part B) with a raw egg, conducting fermentation so that eggshell substantially dissolves into the part B composition, making an opening on an eggshell membrane(s) without substantially affecting the construction of the eggshell membrane(s), and continuing fermentation of the part B composition until appearance of calcium particles on an inner surface of the eggshell membrane(s), 4) combining the part A composition obtained from step 2) and the part B composition obtained from step 3), and introducing thereinto the plant part and a fermentable sugar, so as to form an AB composition wherein casein is located on top of the AB composition, and 5) allowing the AB composition to ferment until a microbial membrane that is capable of growth develops on top of the AB composition and a liquid part forms underneath, and the liquid part is demonstrated antimould activity and has a pH≤about 3.0.

2 Claims, 2 Drawing Sheets

(A)

(B)

ANTIMICROBIAL STRAIN COMPOSITION AND ITS PREPARATION METHOD

TECHNICAL FIELD

The present disclosure relates to antimicrobial strain compositions and to methods for preparing antimicrobial strain compositions. Particularly, the present disclosure relates to antibacterial, antifungal and/or antiviral strain compositions and to methods for preparing them. More particularly, the present disclosure relates to anti-mould strain compositions and to methods for preparing them.

BACKGROUND

An antimicrobial substance is any substance of natural, semisynthetic or synthetic origin that kills or inhibits the growth of microorganisms. Antimicrobial substances mainly include disinfectants (such as bleach), antiseptics, and antibiotics.

Generally, disinfectants, antiseptics, and antibiotics all have slightly different applications. Disinfectants are non-selective and are normally applied to the surface of non-living objects to destroy microorganisms that are living on the objects, antiseptics destroy microorganisms on surfaces of living tissues, for example during surgery, and antibiotics destroy bacteria within a body. Furthermore, antifungals and antivirals are used to respectively target fungi and viruses within and outside a body.

A problem with antibiotics is that they indiscriminately destroy all the susceptible bacteria in an organism and/or microbiome, including both the "bad" bacteria they are targeting and the "good" bacteria that are required to keep the human and animal body healthy. Particularly, the good bacteria can support human and animal health by helping absorb nutrients, digest food, balance blood sugar, regulate the immune system, and balance emotions. Another problem is antibiotic resistance, which occurs when bacteria survive and continue causing infection despite treatment with an antibiotic.

What is currently desirable is an alternative that has less or no impact towards the beneficial microorganisms within a living body while demonstrating inhibitory or killing activity against a wide range of harmful microorganisms. For this purpose, antimicrobial compositions prepared from natural materials have been used in the art. They are used in several industries such as personal care products, food applications, medicine and healthcare. For example, in personal care products, antimicrobials are used to help retard or eliminate the growth of topical pathogens as well as to preserve the personal care products from spoiling or to substantially improve the shelf-life of a product. For example, US2016/0286820 A1 discloses an antimicrobial and antifungal composition for use in personal care products, which is prepared by macerating white fruit of *Cocos Nucifera* to create a feedstock material; mixing the feedstock material with a bacteria and using the bacteria to ferment the feedstock material to create a fermented product; and filtering the fermented product to clarify the product and remove remaining feedstock material and produce the composition, which shows antibacterial and antifungal effectiveness when applied in the personal care products.

However, there remains need for antimicrobial strain compositions prepared from natural materials, which can be used for further culture propagation, so as to provide a composition that has inhibitory or killing activity against a wide range of harmful microorganisms such as bacteria, fungi and/or virus, but causes little or no damage to beneficial microorganisms on the host.

SUMMARY

In a first aspect, the present disclosure provides a method of preparing an antimicrobial strain composition from milk, a raw egg and a plant part, which includes the following steps:
1) providing a dairy composition comprising milk, a fermentable sugar, and edible starters from each of *Lactobacillus*, *Bifidobacterium* and *Acetobacter*,
2) combining a first aliquot of the dairy composition (part A) with *Rhizopus oryzae*, *Aspergillus niger* and/or *Aspergillus oryzae*, and an edible starter from *Saccharomyces*, and conducting fermentation so as to enable the part A composition to substantially turn into a milk curd,
3) combining a second aliquot of the dairy composition (part B) with a raw egg, conducting fermentation so that eggshell substantially dissolves into the part B composition, making an opening on an eggshell membrane(s) without substantially affecting the construction of the eggshell membrane(s), and continuing fermentation of the part B composition until appearance of calcium particles on an inner surface of the eggshell membrane(s),
4) combining the part A composition obtained from step 2) and the part B composition obtained from step 3), and introducing thereinto the plant part and a fermentable sugar, so as to form an AB composition wherein casein is located on top of the AB composition, and
5) allowing the AB composition to ferment until a microbial membrane that is capable of growth develops on top of the AB composition and a liquid part forms underneath, and the liquid part is demonstrated anti-mould activity and has a pH≤about 3.0.

In a second aspect, the present disclosure provides a method for testing if said strain composition prepared by the method of the first aspect and its derivative product have anti-mould activity, which includes adding an amount of the liquid part of the composition or product over yogurt, and placing the liquid part and the yogurt under room temperature and open conditions to observe if mould grows. The derivative product mentioned here means a product that is made from further culture propagation of said strain composition.

In a third aspect, the present disclosure provides an antimicrobial strain composition prepared by the method of the first aspect, which is characterised in that 1) a microorganism membrane is able to develop and thicken therein upon further culture propagation, 2) it has inhibitory or killing activity against harmful microorganisms represented by mould, 3) it is capable of fermenting organic substances, and 4) it is capable of fermenting until pH≤about 3.0.

In a fourth aspect, the present disclosure provides a composition prepared from fermentation of grapes in the strain composition of the third aspect, wherein the fermentation is conducted with a composition comprising a liquid part from the antimicrobial composition, a fermentable sugar, water and grapes until a microbial membrane that is capable of growth develops on top of the composition and a liquid part forms underneath, and the liquid part is demonstrated anti-mould activity and has a pH≤about 3.0.

In a fifth aspect, the present disclosure provides use of a composition of the fourth aspect in health care and/or food preservation.

DESCRIPTION OF EMBODIMENTS

Figure 1:
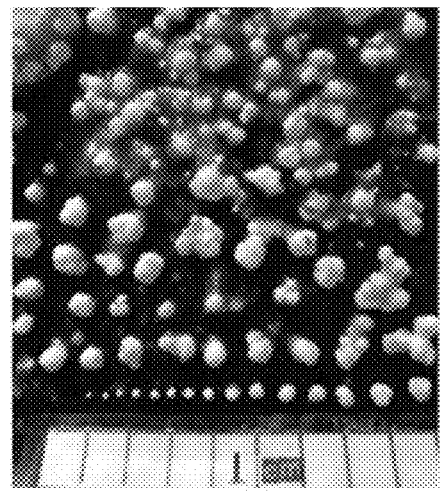
FIG. 1 shows an example of desirable calcium particles (A) and an example of undesirable calcium particles (B).
Figure 1:
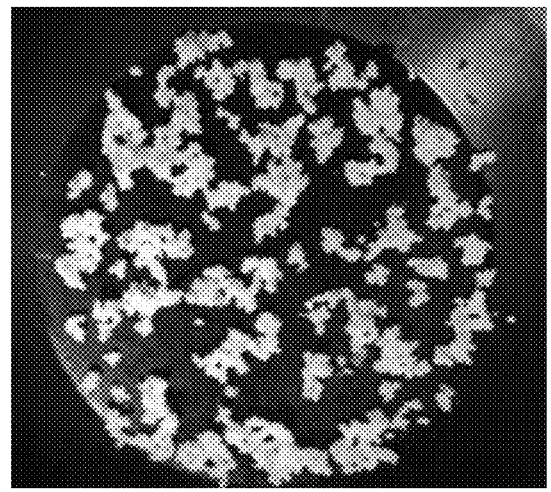

The term "antimicrobial" in the present disclosure means being able to inhibit or kill microorganisms that are harmful to human and/or animal bodies, wherein the microorganisms include, but are not limited to, bacteria, fungi such as mould, and viruses. In some embodiments of the present disclosure, the harmful microorganisms refer to infection-causing microorganisms. In some embodiments of the present disclosure, the harmful microorganisms refer to mould, especially green mould and black mould. In the case of diabetes and diabetes complications, the harmful microorganism may include *Staphylococcus aureus, Enterococcus, Pseudomonas aeruginosa, Escherichia coli, Klebsiella species*, and *Proteus* species. In the case of eczema, the harmful microorganism may include herpes viruses, *Staphylococcus aureus* and Tinea.

The term "strain composition" in the present disclosure means a strain product containing more than one single strain, which can be used for further culture propagation.

In a first aspect, the present disclosure provides a method of preparing an antimicrobial strain composition from milk, a raw egg and a plant part, which includes the following steps:
1) providing a dairy composition comprising milk, a fermentable sugar, and edible starters from each of *Lactobacillus, Bifidobacterium* and *Acetobacter*,
2) combining a first aliquot of the dairy composition (part A) with *Rhizopus oryzae, Aspergillus niger* and/or *Aspergillus oryzae*, and an edible starter from *Saccharomyces*, and conducting fermentation so as to enable the part A composition to substantially turn into a milk curd,
3) combining a second aliquot of the dairy composition (part B) with a raw egg, conducting fermentation so that eggshell substantially dissolves into the part B composition, making an opening on an eggshell membrane(s) without substantially affecting the construction of the eggshell membrane(s), and continuing fermentation of the part B composition until appearance of calcium particles on an inner surface of the eggshell membrane(s),
4) combining the part A composition obtained from step 2) and the part B composition obtained from step 3), and introducing thereinto the plant part and a fermentable sugar, so as to form an AB composition wherein casein is located on top of the AB composition, and
5) allowing the AB composition to ferment until a microbial membrane that is capable of growth develops on top of the AB composition and a liquid part forms underneath, and the liquid part is demonstrated antimould activity and has a pH≤about 3.0.

In respect of the method of the first aspect, it is possible that other substance(s) that will not substantially affect the preparation process may be added or present in the composition. For example, other probiotics, such as probiotics from *Bacillus* can be added or present. Furthermore, in step 1), the dairy composition may contain an amount of freshly-made yogurt.

The term "milk" in the present disclosure can be selected from, for example but not limited to, cow milk, goat milk, sheep milk, and a combination thereof. Furthermore, the milk can be processed or unprocessed. In some embodiments of the first aspect, the milk can be commercially available, for example, milk products sold under the trade mark *PURA*®. Preferably, in addition to the milk, an amount of freshly-made yogurt can be introduced to replace some of the milk.

In some embodiments of the first aspect, the dairy composition substantially consists of milk, a fermentable sugar, and edible starters from each of *Lactobacillus, Bifidobacterium* and *Acetobacter*. In some further embodiments of the first aspect, the dairy composition substantially consists of milk, yogurt, a fermentable sugar, and edible starters from each of *Lactobacillus, Bifidobacterium* and *Acetobacter*.

The phrase "raw egg" used in the present disclosure means eggs that have not been cooked and have eggshell on. The raw egg may be obtained from egg-laying creatures and may include, but not limited to, poultry eggs, for example eggs from laying hens and ducks.

The term "plant" in the present disclosure refers to a fresh plant, and may include, but not limited to, fruit plants. The term "plant part" in the present disclosure may include some part of a plant, for example, but not limited to, branches and leaves of a plant, and seeds and fruits of a plant. In some embodiments of the first aspect, the plant can be fruit grapes. The grapes can be grapes originated from such varieties as Shiraz, Cabernet Sauvignon, Riesling, Chardonnay, Pinot Noir.

The phrase "semi-open condition" in the present disclosure means that the materials to be fermented have certain access to surrounding environment and are not completely open, for the purpose of ventilation and of preventing entry by insects especially drosophila. In this sense, a beneficial bacteria present in the air, such as a yeast bacteria, may participate in fermentation during the procedure of the present method, while a harmful bacteria from the air will be killed. Moreover, the fermentation can be done at room temperature.

The phrase "fermentable sugar" in the present disclosure means a sugar that readily participates in the fermentation of yogurt. The fermentable sugars may include, but not limited to, glucose, fructose, sucrose, maltose, galactose, raffinose and combinations thereof. In some embodiments of the first aspect, the sucrose to be used can originate from for example, but not limited to, cane sugar and beet sugar.

There is no special limitation on the amount of a fermentable sugar for step 1). Generally, the amount of the fermentable sugar for step 1) enables the dairy composition to have an apparent sweet taste. In some embodiments of the first aspect, the amount of the fermentable sugar for step 1) can be at least about 1.0% by weight relative to the weight of the dairy composition. In some embodiments of the first aspect, the amount of the fermentable sugar for step 1) can be at least about 5.0% by weight relative to the weight of the dairy composition. In some other embodiments of the first aspect, the amount of the fermentable sugar for step 1) can be about 10.0% by weight relative to the weight of the dairy composition. In some further embodiments of the first aspect, the amount of the fermentable sugar for step 1) can be about 15.0% by weight relative to the weight of the dairy composition.

The term "*Lactobacillus*" in the present disclosure may include, but not limited to, for example *Lactobacillus casei, Lactobacillus helveticus, Lactobacillus johnsonii, Lactobacillus paracasei, Lactobacillus plantarum, Lactobacillus rhamnosus* and a combination thereof.

The term "*Bifidobacterium*" in the present disclosure may include, but not limited to, for example *Bifidobacterium lactis, Bifidobacterium globosum, Bifidobacterium longum, Bifidobacterium breve, Bifidobacterium bifidum, Bifidobacterium infantis* and a combination thereof.

The term "*Acetobacter*" in the present disclosure may include, but not limited to, for example *Acetobacter pasteurianus, Acetobacter oxydans, Acetobacter schutzenbachii, Acetobacter orleanense, Acetobacter scendens, Acetobacter aceti, Acetobacter xylinum* and a combination thereof.

For step 1), there is no special limitation on the ratio among the starters that come respectively from *Lactobacillus, Bifidobacterium* and *Acetobacter*. For example, the ratio can be about 1:1:1 or 1:2:1. Further, the total amount of the starters can be appropriately varied, as long as it would not have adverse impacts on fermentation in step 2). Specifically, the total amount can be of about 0.1-5.0 wt %, preferably about 1.0-4.0 wt % relative to the weight of the dairy composition.

In step 2), a first aliquot of the dairy composition (part A) is combined with *Rhizopus oryzae, Aspergillus niger* and/or *Aspergillus oryzae*, and an edible starter from *Saccharomyces*, and fermentation is conducted so as to enable the part A composition to substantially turn into a milk curd. The fermentation can be carried out under semi-open conditions. Further, a fermentable sugar can be added if needed. In some embodiments of the first aspect, fermentation in step 2) can be conducted at a temperature of about 22° C. to about 32° C., such as about 22° C., about 23° C., about 24° C., about 25° C., about 26° C., about 27° C., about 28° C., about 29° C., about 30° C., about 31° C., or about 32° C. In some embodiments of the first aspect, fermentation in step 2) can be conducted at room temperature. In some embodiments of the first aspect, fermentation in step 2) is conducted until the milk curd has a pH of about 4.0 to about 4.5.

For step 2), the fermentation enables the part A composition to substantially turn into a milk curd. In other words, the fermentation enables at least about 95 wt %, preferably at least about 98 wt %, more preferably about 100 wt % of the part A composition to turn into a milk curd.

The phrase "an edible starter from *Saccharomyces*" in the present disclosure includes yeasts typically used by brewers (for example for brewing wines, beers, liquors, spirits) and by bakers (for example for baking bread). Specifically, examples may include, but not limited to, *Saccharomyces cerevisiae, Saccharomyces bayanus, Saccharomyces carlsbergensis, Saccharomyces boulardii, Saccharomyces eubayanus*, and a combination thereof.

The total amount of *Rhizopus oryzae, Aspergillus niger* and/or *Aspergillus oryzae*, and an edible starter from *Saccharomyces* used in step 2) can be about 0.5~8 wt %, preferably about 0.8~5 wt % relative to the amount of the Part A composition. The ratio among *Rhizopus oryzae, Aspergillus niger* and/or *Aspergillus oryzae*, and an edible starter from *Saccharomyces* may appropriately vary, which can be, for example, 1:1:1 or 2:1:2.

For step 3), a first aliquot of the dairy composition (part B) is combined with a raw egg, and allowed to ferment so that eggshell substantially dissolves into the part B composition, an opening is made on an eggshell membrane(s) without substantially affecting the construction of the eggshell membrane(s), and fermentation of the part B composition is continued until the appearance of calcium particles on an inner surface of the eggshell membrane(s). The fermentation can be carried out under semi-open conditions. The number of the raw eggs to be added enables the appearance of calcium particles as shown in FIG. 1(A)) on an inner surface the eggshell membrane(s) through fermentation after the eggshell substantially dissolves into the part B composition and an opening is made on the eggshell membrane(s). The calcium particles shown in FIG. 1(B)) are not desirable, which may appear when adding merely eggshells and/or adding a cooked egg. The calcium particles as shown in FIG. 1(A) are characterised in formation on an inner surface of the eggshell membrane(s), being substantially rounded, and capable of growth. Preferably, an opening is made on the eggshell membrane(s) (for example by poking with a knife) immediately after the eggshell is fully dissolved into the part B composition. In some embodiments of the first aspect, fermentation in step 3) can be conducted at a temperature of about 22° C. to about 32° C., such as about 22° C., about 23° C., about 24° C., about 25° C., about 26° C., about 27° C., about 28° C., about 29° C., about 30° C., about 31° C., or about 32° C. In some embodiments of the first aspect, fermentation in step 3) can be conducted at room temperature.

In some embodiments of the first aspect, the part A composition and the part B composition taken from the dairy composition can be a half amount of the dairy composition respectively. In some other embodiments of the first aspect, the part A composition and the part B composition taken from the dairy composition can be some of the dairy composition respectively, and the weight ratio between the part A composition and the part B composition is about 1:1.

For step 4), the part A composition obtained from step 2) is combined with the part B composition obtained from step 3), introducing thereinto the plant part and a fermentable sugar, so as to form an AB composition wherein casein is located on top of the AB composition. The plant part needs no cleaning, and the bacteria remaining thereon might assist in the fermentation of step 5). For step 4), in order for casein to be located on top of the AB composition, a fermentable sugar is introduced until 10 wt % up to saturated relative to the total amount of the part A composition and the part B composition. Preferably, a fermentable sugar is introduced until saturated relative to the total amount of the part A composition and the part B composition. It is important that addition of a fermentable sugar enables casein to be located on top of the AB composition and milk whey to be located underneath.

For step 5), the AB composition is fermented until a microbial membrane that is capable of growing develops on top of the AB composition and a liquid part forms underneath, and the liquid part demonstrates anti-mould activity and has a pH≤about 3.0, preferably≤about 2.5, more preferably≤about 2.0. The fermentation can be carried out under semi-open conditions. In some embodiments of the first aspect, fermentation in step 5) can be conducted at a temperature of about 22° C. to about 32° C., such as about 22° C., about 23° C., about 24° C., about 25° C., about 26° C., about 27° C., about 28° C., about 29° C., about 30° C., about 31° C., or about 32° C. In some embodiments of the first aspect, fermentation in step 5) can be conducted at room temperature. Then a desirable strain composition is prepared, which is characterised in that 1) a microorganism membrane is able to develop and thicken therein upon further culture propagation, 2) it has inhibitory or killing activity against harmful microorganisms represented by mould, 3) it is capable of fermenting organic substances, and 4) it is capable of fermenting until pH≤about 3.0. Generally, the microbial membrane is of white colour, smooth and glossy, and is capable of growth, for example in thickness. Relatively stronger acidic conditions are favourable in terms of the fermentation in step 5). It is important to determine if the liquid part becomes anti-mould during the fermentation process, which can be carried out by the method as described later.

The term "anti-mould" in the present disclosure intends to be associated with organic substances and means the killing or inhibitory activity against mould, for example green mould and black mould. This activity can be measured against mould through the method described hereinafter. The organic substances include, but not limited to, various food such as water, yogurt and fruits.

In some embodiments of the present disclosure, the anti-mould activity test is used to determine if said strain composition or its derivative product has inhibitory or killing activity against harmful microorganisms that are represented by mould. Various substrates such as yogurt can be used to conduct the test. Several identical containers that have a certain amount of yogurt are prepared, and then a layer of the substance to be tested is spread to cover the surface of the yogurt, wherein the thickness of the substance to be tested can be for example about 0.5 to 1 cm. The substance to be tested includes the liquid part obtained from step 5) in the method of the first aspect. In addition, a control experiment can be carried out. The control substance to be tested can include, for example, water. All the samples are then placed under open conditions at room temperature. With the progress of evaporation, mould together with other harmful microorganisms may grow out. If there is no growth of mould together with other harmful microorganisms after a period of time, it is preliminarily believed that the substance to be tested has anti-mould activity. Furthermore, it is possible to evaluate the anti-mould activity of the substance to be tested according to the speed of growth of mould and/or the sizes and number of microorganism spots.

In a third aspect, the antimicrobial strain composition is characterised in that 1) a microorganism membrane is able to develop and thicken therein upon further culture propagation, 2) it has inhibitory or killing activity against harmful microorganisms represented by mould, 3) it is capable of fermenting organic substances, and 4) it is capable of fermenting until pH≤about 3.0.

In relation to the fourth aspect, the strain composition can be used to enable further fermentation of grapes, so as to provide a composition that has inhibitory or killing activity against a wide range of harmful microorganisms such as bacteria, fungi and/or viruses, but causes little or no damage to the beneficial microorganisms on the host. The fermentation is conducted with a composition comprising a liquid part from the antimicrobial strain composition, a fermentable sugar, water and grapes until a microbial membrane that is capable of growth develops on top of the composition and a liquid part forms underneath, and the liquid part is demonstrated anti-mould activity and has a pH≤about 3.0. The fermentation can be carried out under semi-open conditions. In some embodiments of the fourth aspect, fermentation can be conducted at a temperature of about 22° C. to about 32° C., such as about 22° C., about 23° C., about 24° C., about 25° C., about 26° C., about 27° C., about 28° C., about 29° C., about 30° C., about 31° C., or about 32° C. In some embodiments of the fourth aspect, fermentation can be conducted at room temperature. In some embodiments of the fourth aspect, the fermentation is conducted with a composition consisting of a liquid part from the antimicrobial strain composition, a fermentable sugar, water and grapes. In some embodiments of the fourth aspect, the fermentation can be carried out with a liquid part from the antimicrobial strain composition and water containing a fermentable sugar in a ratio of about 1:1 by weight as well as an amount of grapes. The amount of grapes may be chosen in accordance with the fermenter to be used. The composition obtained thereby can serve as a starting strain for long-term propagation.

In a fifth aspect, the present disclosure provides the use of the composition of the fourth aspect in health care and/or food preservation. It is believed that the components in the composition of the fourth aspect have synergistic effects, can obviously promote the internal metabolism, and maintain beneficial microflora in the intestines. In some embodiments, the composition can be used to alleviate or improve symptoms, for example, ovarian cancer, type II diabetes and complications, as well as eczema and skin scars.

EXAMPLES

Example 1—Preparation of the Antimicrobial Strain Composition

2 L milk, such as original milk sold under the trademark PURA®, 200 g sucrose and 45 g *Lactobacillus casei*, *Bifidobacterium lactis* and *Acetobacter oxydans* (about 1:1:1 by weight) were added into 3 L fermenter, so as to provide a dairy composition. A half of the dairy composition (part A) is combined with 12 g *Saccharomyces cerevisiae*, *Rhizopus oryzae* and *Aspergillus niger* (about 1:1:1 by weight), and then fermented under semi-open conditions at room temperature to produce a part A that has substantially turned into a milk curd. The other half of the dairy composition (part B) is combined with 4 raw chicken eggs, and then fermented under semi-open conditions until the eggshell is fully dissolved into the part B composition. Eggshell membranes are then poked with a knife without substantially affecting the construction of the eggshell membrane(s) and fermentation of the part B composition is continued until appearance of calcium particles on an inner surface of the eggshell membranes. The part A composition having substantially turned into a milk curd is combined with the part B composition having calcium particles therein. Sucrose is added therein until saturated, and Shiraz grapes of 0.5 kg are also added therein, so as to form an AB composition wherein casein is located on top of the AB composition. The AB composition is fermented at room temperature under semi-open conditions until a microbial membrane that is capable of growth appears on top of the AB composition and a liquid part forms underneath, and the liquid part is tested to be anti-mould and has a pH of about 3.0.

Example 2—Anti-Mould Activity Test

Figure 2:
FIG. 2 shows yogurt samples respectively treated by water and by the liquid part of the strain composition obtained from Example 1.

The method is described below with yogurt as a substrate. A certain amount of plain yogurt is poured into four identical containers separately. A 1 cm thick layer of the liquid part obtained from Example 1 or a 1 cm thick layer of water is spread over to cover the surfaces in the containers respectively. The containers are then kept at room temperature and open conditions. With the progress of evaporation, mould grows out within the container treated by water. It is surprisingly observed that no mould appears in the container that has been treated with the liquid part obtained from Example 1, even if during summer. If any, mould normally occurs within about 5-10 days after treatment. The results are shown in FIG. 2. The sample on the left has been treated by water and left uncovered, while the sample on the right has been treated by the liquid part obtained from Example 1 and left uncovered.

Example 3—Anti-Mould Activity

Figure 3:
FIG. 3 shows commercially available yogurt samples that have been respectively treated by water and by the liquid part of the strain composition obtained from Example 1.

The anti-mould activity test in Example 2 was conducted on yogurt samples available from supermarkets in Melbourne and Adelaide, Australia. The results are shown in FIG. 3. The samples located in the second and fourth rows from the top were treated by the liquid part obtained from Example 1, and demonstrated anti-mould activity.

Example 4—Uses of a Composition Obtained from Fermentation/Propagation of the Antimicrobial Strain Composition An antimicrobial composition was prepared through further fermentation of grapes within a liquid part of the strain composition obtained from Example 1. The fermentation was conducted as follows: introducing 500 g of the liquid part obtained from Example 1, 500 g water having 10 wt % sucrose therein and 100 g grapes into a fermenter so as to form a composition, and allowing the composition to ferment under semi-open conditions at room temperature until a microbial membrane that is capable of growth develops on top of the composition and a liquid part forms underneath, and the liquid part is demonstrated anti-mould activity and has a pH≤about 3.0.

Treatment Effects on Type II Diabetes

| Patient | Age | Period for oral administration of the composition | Glycemic index (Generally, lower value is taken before meal, and high value is taken after meal) | |
|---|---|---|---|---|
| | | | before treatment | after treatment |
| A | 71 | 4.5 months | 14.2-17.9 | 6.7 |
| B | 59 | 2 months | 9.7-13.4 | 5.8-6.4 |
| C | 59 | 1.5 months | 10.9-15.3 | 5.7-6.1 |
| D | 42 | 1.5 months | 9.7-13.4 | 5.4-6.4 |

Treatment Effects on Diabetes-Related Complications

Patient E suffered diabetes-related complications for about 1 year such as painful footfingers and visible pus-filled sores. On the first day of administration of the composition prepared as above on his feet, pus discharged out of the sores. After 20 consecutive days of such administration, a scab was formed on his wound and his wound swelling underwent apocatastasis. A medical test showed that no bacterium was contained in the pus, but some bacteria existed in his bones. However, an administration of antibiotics during 14 days afterwards did not produce substantial alleviation, instead, brought him many side effects such as dizziness, uncomfortable heart condition, constipation, anal projection and back pain etc. Then the patient resumed administration of the composition as prepared above for over 6 months and surprisingly found that those side effects disappeared and the glycemic index was stabilised at 4.2-6.2. Notably, this helped avoid the case that his foot wounds fester to the point that his feet needed to be amputated.

Treatment Effects on Ovarian Cancer

Patient F was diagnosed with stage IV ovarian cancer on 9 Jul. 2016. She felt weak all over and had a loss of appetite. Despite chemotherapy treatment for one year, her symptoms deteriorated. However, after treatment with the composition as prepared above, her condition improved. It is noted that a normal range for cancer cell index in blood is 0-35.

| Date | Condition | Cancer cell index in blood (Normal value 0-35) | Chemotherapy | Effect |
|---|---|---|---|---|
| 9 Jul. 2016 | Diagnosed as stage IV ovarian cancer | | | |
| 6 Aug. 2016 | | | 6 times of chemotherapy | |
| 1 Dec. 2016 | | | | |
| 13 Feb. 2017 | | 19 | | |
| 9 Jun. 2017 | Cancer recurrence | 167 | | |
| 6 Sep. 2017 | Ascites | 378 | | |
| 9 Dec. 2017 | Ascites | 1529 | | |
| 3 Jan. 2018 | Pumping ascites of 14 lb | | | |
| 5 Jan. 2018 | | 1415 | | |
| 11 Jan. 2018 | Pumping ascites of 20 lb | | | |
| 29 Jan. 2018 | | 2670 | | |
| 1 Feb. 2018 | | | | |
| 8 Feb. 2018 | | | | |
| 15 Feb. 2018 | Administration of the antimicrobial composition | | | |

-continued

| Date | Condition | Cancer cell index in blood (Normal value 0-35) | Chemotherapy | Effect |
|---|---|---|---|---|
| 22 Feb. 2018 | | 509 | | The antimicrobial composition can help reduce the abdominal pain. Her appetite had substantial improvement. |

It will be appreciated by those skilled in the art that the disclosure is not restricted in its use to the particular application described. Neither is the present disclosure restricted in its preferred embodiment with regard to the particular elements and/or features described or depicted herein. It will be appreciated that the disclosure is not limited to the embodiment or embodiments disclosed, but is capable of numerous rearrangements, modifications and substitutions without departing from the scope of the disclosure as set forth and defined by the following claims.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

The invention claimed is:

1. A method of preparing an antimicrobial strain composition from milk, a raw egg and a plant part, which includes the following steps:
   1) providing a dairy composition comprising milk, a fermentable sugar, and edible starters from each of *Lactobacillus*, *Bifidobacterium* and *Acetobacter*,
   2) combining a first aliquot of the dairy composition (part A) with *Rhizopus oryzae*, *Aspergillus niger* and/or *Aspergillus oryzae*, and an edible starter from *Saccharomyces*, and conducting fermentation so as to enable the part A composition to substantially turn into a milk curd,
   3) combining a second aliquot of the dairy composition (part B) with a raw egg, conducting fermentation so that the eggshell substantially dissolves into the part B dairy composition, making an opening on the eggshell membrane without substantially affecting the construction of the eggshell membrane, and continuing fermentation of the part B composition until calcium particles appear on an inner surface of the eggshell membrane,
   4) combining the part A composition obtained from step 2) and the part B composition obtained from step 3), and introducing thereto the plant part and more fermentable sugar, so as to form an AB composition wherein casein is located on top of the AB composition, and
   5) allowing the AB composition to ferment until a microbial membrane that is capable of growth develops on top of the AB composition and a liquid part forms underneath, and the liquid part has a pH 3.0.

2. A method for testing if the strain composition prepared according to claim 1 has anti-mould properties, which includes adding an amount of the liquid part of the strain composition over yogurt, and placing the liquid part and the yogurt under room temperature and open condition to observe if mould grows.

* * * * *